(12) United States Patent
Chevalier

(10) Patent No.: US 6,294,375 B1
(45) Date of Patent: Sep. 25, 2001

(54) MICROBIOLOGICAL PRESSURIZED GAS CONTROL DEVICE

(75) Inventor: Philippe Chevalier, deceased, late of Garancieres (FR), by Mathieu Chevalier, Christophe Chevalier, heirs

(73) Assignee: Ultra Propre Nutrition Industrie Recherche (U.N.I.R.), Paris (FR)

( * ) Notice: Subject to any disclaimer, the term of this patent is extended or adjusted under 35 U.S.C. 154(b) by 0 days.

(21) Appl. No.: 08/930,675

(22) PCT Filed: Apr. 3, 1996

(86) PCT No.: PCT/FR96/00506

§ 371 Date: Nov. 4, 1998

§ 102(e) Date: Nov. 4, 1998

(87) PCT Pub. No.: WO96/31594

PCT Pub. Date: Oct. 10, 1996

(30) Foreign Application Priority Data

Apr. 6, 1995 (FR) .................................................. 95 04107

(51) Int. Cl.[7] .............................. C12M 1/26; C12M 1/22
(52) U.S. Cl. ................................. 435/287.1; 435/287.9; 435/288.3; 435/309.1; 73/28.05
(58) Field of Search ................................... 435/30, 287.1, 435/287.5, 287.7, 287.9, 288.3, 297.5, 305.1, 305.4, 308.1, 309.1; 73/28.04, 28.05, 28.06, 863.22, 863.23, 864.71

(56) References Cited

U.S. PATENT DOCUMENTS

| 2,894,877 | 7/1959 | Sinden . | |
|---|---|---|---|
| 3,001,914 | * 9/1961 | Andersen . | |
| 4,038,057 | * 7/1977 | Roth . | |
| 4,255,172 | 3/1981 | Smith | ..................... 55/270 |
| 4,274,846 | 6/1981 | Smith | ..................... 55/270 |
| 5,693,895 | * 12/1997 | Baxter . | |

FOREIGN PATENT DOCUMENTS

| 0 450 850 A2 | 10/1991 | (EP) . |
|---|---|---|
| 2 469 452 | * 5/1981 | (FR) . |
| 2224118 A | 4/1990 | (GB) . |

* cited by examiner

Primary Examiner—William H. Beisner
(74) Attorney, Agent, or Firm—Finnegan, Henderson, Farabow, Garrett, & Dunner, L.L.P.

(57) ABSTRACT

A device for microbiologically controlling a dust-laden pressurized gas, including dust collecting device in an inner cavity provided with a gas inlet and a gas outlet and having an internal pressure that is equal to the pressure of said dust-laden gas at least during the operation of said device.

12 Claims, 1 Drawing Sheet

MICROBIOLOGICAL PRESSURISED GAS CONTROL DEVICE

Figure 1:
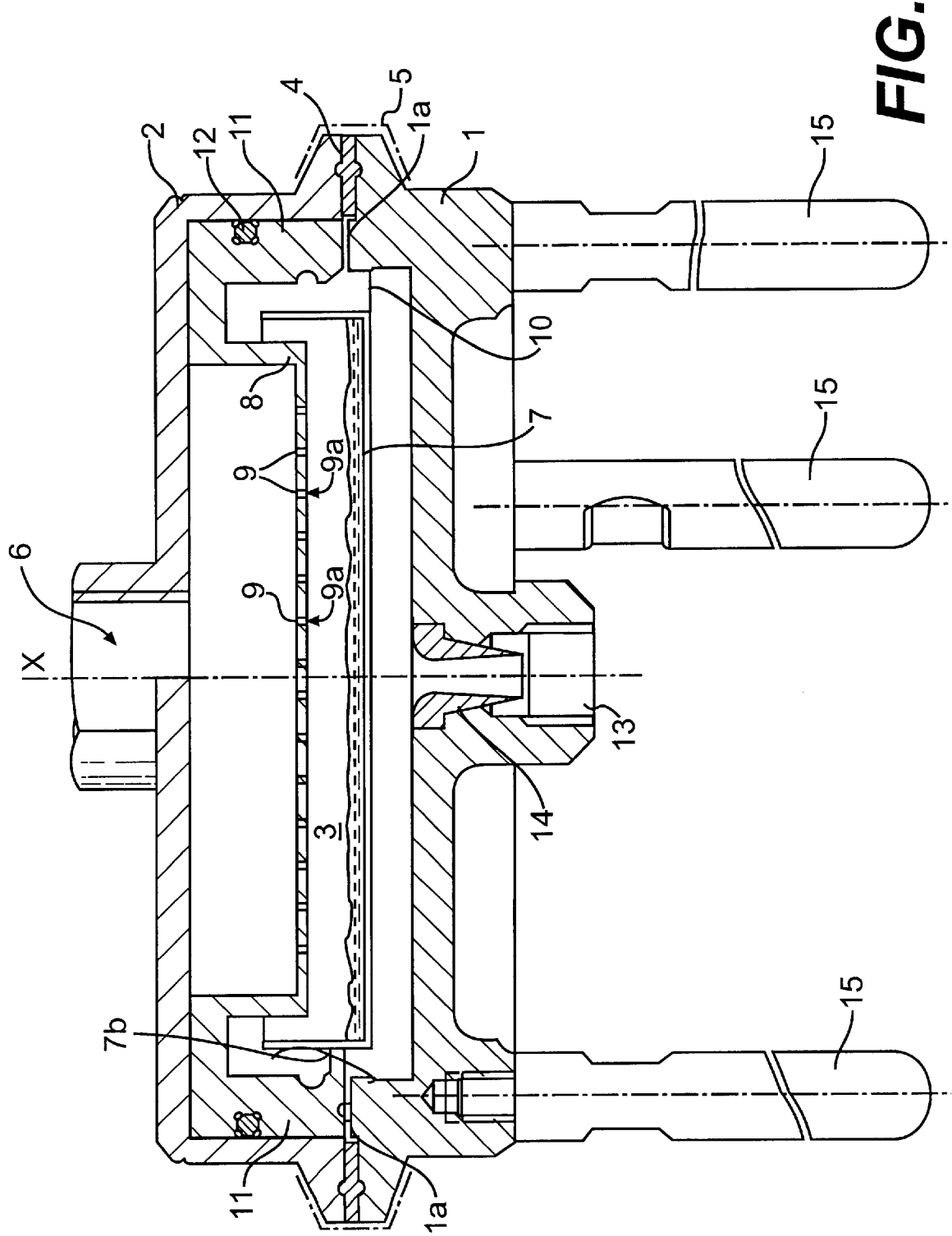

The present invention relates to a microbiological pressurised gas control device.

One particularly beneficial application of the invention is the control of compressed air or oxygen for example circulating in a network, such as a network supplying surgical or treatment units in hospitals, or clean rooms used in the pharmaceutical and cosmetic industries and in the agro-food industry.

Microbiological control devices for environmental air using the principle of impaction are already known.

In these known devices, a Petri dish placed facing an impaction plate pierced with numerous small holes, subsequently called a "filter", is used to collect the dust particles contained in the environmental air which is aspirated by a pump through the perforations of the filter, the jets crossing through the perforations of the filter being projected onto the nutrient medium of the Petri dish.

The micro-organisms contained in the dust impacted by the jets of gas onto the nutrient medium, multiply and produce colonies if the nutrient medium is suitable. After several days of incubation, these germs are therefore replaced by visible colonies of which some can be identified by the naked eye.

The control of a pressurised gas using known devices requires prior pressure release of the gas initially compressed at several bars, which usually leads to a sonic burst followed by a shock wave. These sharp variations in gas pressure cause the destruction of the micro-organisms contained in the dust particles carried by the gas. Measurements taken on the released gas are therefore not representative measurements of the biocontamination of said gas.

The present invention describes a new microbiological control device for a pressurised gas carrying dust particles, without causing the total or partial destruction of the micro-organisms contained in said dust particles.

More particularly, the device of the invention comprises collection means for collecting said dust particles contained in the pressurised gas, said collection means being placed in an inner cavity fitted with a gas inlet and a gas outlet, and in which the prevailing gas pressure is, at least during the operation of said device, equal to the pressure of the gas carrying dust particles entering said cavity.

Therefore, such device may advantageously be directly connected to a supply network of compressed gas, or to the outlet of a container containing such gas.

According to one beneficial characteristic of the device according to the invention, it comprises a sonic nozzle positioned at the exit of said cavity, downstream from said collection means.

Said sonic nozzle is used to release the pressure of the gas that is pressurised in said device, reducing it to atmospheric pressure while maintaining constant volume flow. This is advantageous as, regardless of pressure, the device of the invention can achieve identical volume flow at impaction level.

Needless to say the diameter of the sonic nozzle can be adapted in relation to desired volume flow.

The description given below with reference to the appended drawing given as a non-restrictive example, will give a full understanding of the content of this invention and how it can be implemented.

The single FIGURE is an axial section view of a microbiological pressurised gas control device in accordance with the invention.

The FIGURE shows a microbiological pressurised gas control device such as compressed air for example or compressed oxygen.

This device comprises a casing 1 closed with a lid 2 in such manner as to form an inner cavity 3 that essentially rotates around a central axis X. Lid 2 is closed in sealed manner on casing 1 by means of a ring seal 4 and a conventional circlip 5. Lid 2 comprises an opening 6 centrally aligned with axis X of the cavity. In said opening 6 a valve is provided (not shown in this FIGURE) which can be connected for example to a supply network of a pressurised gas. Opening this valve allows the gas to enter said cavity 3.

In addition, casing 1 comprises inner fittings used to position a standard Petri dish, with a diameter of 90 mm for example, perpendicular to axis X and facing opening 6, and above said Petri dish 7 to position a perforated impaction plate 8 subsequently called a "filter". Petri dish 7 is filled with approximately 16 ml of nutrient medium, called agar. The distance between outlets 9a of perforations 9 of filter 8 and the surface of the agar is defined in relation to the size d of perforations 9a.

Perforations 9 are made in filter 8 in such manner that the axis of perforations 9 is essentially directed in perpendicular fashion towards the base of Petri dish 7. Perforations 9 lead to the base of Petri dish 7. The sizes of said perforations 9 and the number of perforations 9 of filter 8 are determined in relation to the required speed of the jet of gas crossing through each perforation. This speed is dependent upon the diameter of the dust particles that it is wished to collect in the Petri dish.

To collect dust as fine as possible, it is advisable that the jets of gas carrying said dust particles should follow a very tight bend on exiting perforations 9 of filter 8, which necessitates perforations of small diameter. Therefore, the jets of compressed gas exiting said perforations 9 fall on the nutrient medium of Petri dish 7 along a pathway with a very slight curve radius and at high speed so that these fine dust particles are projected directly onto the nutrient medium of Petri dish 7. However, the speed with which the dust particles are projected onto the nutrient medium of Petri dish 7 must not be too high as the micro-organisms contained in the dust particles might suffer stress under the violent impact on the nutrient medium and have difficulty in reproducing and forming a colony in the nutrient medium.

For the above-mentioned reasons, the recommended speed of the jets of compressed gas exiting the perforations of the filter is in the region of 20 metres per second. This requires a perforation for filter 8 of approximately 600 holes of 0.4 mm in diameter in order to obtain a flow of approximately 100 liters per minute. The diameter of filter 8 is substantially equal to that of the Petri dish, in this example 90 mm. Distance h between the agar surface and filter 8 is approximately between 2d and 6d.

According to the embodiment illustrated, Petri dish 7 is placed on support tabs of a leaf spring 10 (in this example three support tabs distanced around the circumference of Petri dish 7 of which only one is shown) placed in the bottom of cavity 3 formed by casing 1. Filter 8 is suspended from a support 11 (in this case forming a single part with said casing) positioned in an indentation 1a of said casing 1. Leaf support 10 comprises adjuster fastening 7b (of which only is shown) which extend cross-wise to axis X as far as support 11 and are held in place by the latter. The seal between said support 11 and lid 2 is made by a topic seal 12.

It is of interest to specify that the volume of inner cavity 3 located below the collection means formed by filter 8 and Petri dish 7 is of minimum size. In the example shown, this volume is approximately 30 cm³. On the other hand, the volume of the cavity lying between filter 8 and inlet 6 to cavity 3 is not determinant.

Cavity 3 comprises a gas outlet 13 towards the outside provided in casing 1. This outlet 13 is aligned with axis X. A sonic nozzle 14 is positioned downstream from Petri dish 7 upstream from gas outlet 13. More particularly, sonic nozzle 14 is positioned in line with axis X in an inner recess of casing 1 and leads directly into gas outlet 13.

According to the embodiment illustrated, casing 1 is placed on leg supports 15.

Said device operates in the following manner.

Opening 6 of lid 2 is connected to a gas supply under pressure so that opening of the valve causes the entry of pressurised gas into cavity 3. This pressurised gas then crosses through filter 8 through perforations 9 and at the exit of filter 8 projects the dust particles it contains onto the nutrient medium of Petri dish 7, and subsequently escapes through the sides of Petri dish 7. The pressurised gas is therefore evacuated to the outside via sonic nozzle 14. When the device is in operation, the pressure prevailing inside inner cavity 3 is equal to the pressure of the pressurised gas crossing through it. Sonic nozzle 14 releases the pressure of the gas arriving under pressure until it reaches atmospheric pressure while maintaining a constant volume flow after release and in particular a constant volume flow at the impaction level of the dust particles on the nutrient medium. This is beneficial since it is this volume flow which determines impaction properties.

The dust particles collected with this device have a diameter of more than 0.5 $\mu$m.

The gas flow with said device may vary between approximately 10 and 1000 liters per minute in relation to the number and diameter of the filter perforations.

Needless to say, the present invention is not restricted to the embodiment described and illustrated; men of the art may make any variant thereto in line with the spirit of the invention. In particular, fixation means other than the leaf spring and adjuster fastening may be considered for the Petri dish, such as for example hooks mounted in the inner wall of the casing. Also, it is possible to consider assembling certain parts of the device in a single block.

What is claimed is:

1. Microbiological pressurised gas control device carrying dust particles comprising a casing forming an inner cavity: collection means to collect said dust particles placed in said inner cavity fitted with a gas inlet and outlet and in which the prevailing pressure is, at least during the operation of said device, equal to the pressure of said gas carrying dust particles; and a sonic nozzle downstream from said collection means and placed at said gas outlet of said cavity.

2. The device in accordance with claim 1, wherein the volume of said cavity lying between said collection means and said gas outlet is of minimum size and in the region of 30 $cm^3$.

3. The device in accordance with claim 2, comprising a lid closing said casing and inner cavity in a sealed manner, said casing being provided with inner fittings to carry said collection means.

4. The device in accordance with claim 3, wherein said collection means comprise a Petri dish placed in said inner cavity, containing a nutrient medium facing said inlet into said cavity and a perforated impaction plate placed above said Petri dish parallel to the latter.

5. The device in accordance with claim 4, wherein said impaction plate comprises approximately 600 perforations leading towards the base of said Petri dish, said perforations having a diameter of approximately 0.4 mm.

6. The device in accordance with claim 5, wherein the distance between the surface of the nutrient medium placed in said Petri dish and the position of said impaction plate is determined in relation to the sizes of said perforations of said impaction plate, such that said distance is between two times and six times the diameter of said perforations.

7. The device in accordance with claim 4, wherein the distance between the surface of the nutrient medium placed in said Petri dish and the position of said impaction plate is determined in relation to the sizes of said perforations of said impaction plate, such that said distance is between two times and six times the diameter of said perforations.

8. The device in accordance with claim 1, comprising a a lid closing said casing and inner cavity in a sealed manner, said casing being provided with inner fittings to carry said collection means.

9. The device in accordance with claim 8, wherein said collection means comprise a Petri dish placed in said inner cavity, containing a nutrient medium facing said inlet into said cavity and a perforated impaction plate placed above said Petri dish parallel to the latter.

10. The device in accordance with claim 9, wherein said impaction plate comprises approximately 600 perforations leading towards a base of said Petri dish, said perforations having a diameter of approximately 0.4 mm.

11. The device in accordance with claim 10, wherein the distance between the surface of the nutrient medium placed in said Petri dish and the position of said impaction plate is determined in relation to the sizes of said perforations of said impaction plate, such that said distance is between two times and six times the diameter of said perforations.

12. The device in accordance with claim 9, wherein the distance between the surface of the nutrient medium placed in said Petri dish and the position of said impaction plate is determined in relation to the sizes of said perforations of said impaction plate, such that said distance is between two times and six times the diameter of said perforations.

* * * * *

UNITED STATES PATENT AND TRADEMARK OFFICE
CERTIFICATE OF CORRECTION

PATENT NO. : 6,294,375 B1
DATED : September 25, 2001
INVENTOR(S) : Philippe Chevalier et al.

It is certified that error appears in the above-identified patent and that said Letters Patent is hereby corrected as shown below:

Column 3, claim 1,
Line 42, "pressurised" should read -- pressurized --.

Column 4, claim 5,
Line 12, "the base" should read -- a base --.

Column 4, claim 8,
Line 27, "comprising a a" should read -- comprising a --.

Signed and Sealed this

Twenty-sixth Day of February, 2002

Attest:

Attesting Officer

JAMES E. ROGAN
Director of the United States Patent and Trademark Office